US012209730B2

(12) United States Patent
Van Bommel et al.

(10) Patent No.: US 12,209,730 B2
(45) Date of Patent: Jan. 28, 2025

(54) CEILING SUSPENDED LIGHTING UNIT

(71) Applicant: SIGNIFY HOLDING B.V., Eindhoven (NL)

(72) Inventors: Ties Van Bommel, Horst (NL); Rifat Ata Mustafa Hikmet, Eindhoven (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 18/576,871

(22) PCT Filed: Jun. 17, 2022

(86) PCT No.: PCT/EP2022/066596
§ 371 (c)(1),
(2) Date: Jan. 5, 2024

(87) PCT Pub. No.: WO2023/280548
PCT Pub. Date: Jan. 12, 2023

(65) Prior Publication Data
US 2024/0384844 A1    Nov. 21, 2024

(30) Foreign Application Priority Data
Jul. 6, 2021    (EP) .................................... 21183918

(51) Int. Cl.
*F21S 8/02*        (2006.01)
*A61L 9/20*        (2006.01)
(Continued)

(52) U.S. Cl.
CPC ................. *F21S 8/026* (2013.01); *A61L 9/20* (2013.01); *A61L 9/22* (2013.01); *F21V 21/048* (2013.01);
(Continued)

(58) Field of Classification Search
CPC ....... F21S 8/026; F21V 21/048; F21V 21/049
See application file for complete search history.

(56) References Cited

U.S. PATENT DOCUMENTS 10,663,148 B1    5/2020   Heredia
2006/0262521 A1  11/2006  Piepgras et al.
(Continued)

FOREIGN PATENT DOCUMENTS

CN    203477966 U    3/2014
CN    208202291 U    12/2018
(Continued)

*Primary Examiner* — Sean P Gramling

(57) ABSTRACT

The present invention generally relates to the field of a lighting unit (100), and in particular to a lighting unit (100) that is suitable for being part of a suspended ceiling (0001). The lighting unit (100) comprises one or more lighting tiles (1000) and an interface component (2000). The interface component (2000) forms at least a portion of a grid system (1020) for the suspended ceiling (0001) and for supporting the lighting tile (1000). The interface component (2000) comprises a central support portion (2001) having a first end (2002) facing a ceiling (0002), and a second end (2003) having a first flange (2004) and a second flange (2005) that are opposing each other. At least one of the first flange (2004) and the second flange (2005) comprises a through-hole (2006) that serves as an aperture for at least part of a device (1001) that is arranged at one of the peripheries (1002, 1003) of the lighting tile (1000) when the first flange (2004) is configured to support a first lighting tile when the first lighting tile is installed in the suspended ceiling (0001) and/or the second flange (2005) is configured to support a second lighting tile when the second lighting tile is installed in the suspended ceiling (0001).

12 Claims, 7 Drawing Sheets

(51) Int. Cl.
    *A61L 9/22*         (2006.01)
    *F21V 21/04*       (2006.01)
    *F21V 23/04*       (2006.01)
    *F21V 33/00*       (2006.01)
    *F21Y 113/00*     (2016.01)

(52) U.S. Cl.
    CPC ...... F21V 23/0442 (2013.01); F21V 33/0064 (2013.01); *A61L 2209/111* (2013.01); *A61L 2209/12* (2013.01); *A61L 2209/15* (2013.01); *F21Y 2113/30* (2023.05)

(56) References Cited

U.S. PATENT DOCUMENTS

| | | | |
|---|---|---|---|
| 2008/0266843 | A1 | 10/2008 | Villard |
| 2011/0175533 | A1* | 7/2011 | Holman ............... F21S 2/00 |
| | | | 362/147 |
| 2016/0076746 | A1 | 3/2016 | Porciatti |
| 2020/0173639 | A1 | 6/2020 | Martin |

FOREIGN PATENT DOCUMENTS

| | | | |
|---|---|---|---|
| CN | 111663705 | A | 9/2020 |
| CN | 112576983 | A | 3/2021 |
| CN | 213431894 | U | 6/2021 |
| EP | 2650599 | A1 | 10/2013 |
| TW | M513332 | U | 12/2015 |
| WO | 2010042216 | A2 | 4/2010 |
| WO | 2013149679 | A1 | 10/2013 |

\* cited by examiner

CEILING SUSPENDED LIGHTING UNIT

CROSS-REFERENCE TO PRIOR APPLICATIONS

This application is the U.S. National Phase application under 35 U.S.C. § 371 of International Application No. PCT/EP2022/066596, filed on Jun. 17, 2022, which claims the benefit of European Patent Application No. 21183918.8, filed on Jul. 6, 2021. These applications are hereby incorporated by reference herein.

FIELD OF THE INVENTION

The present invention generally relates to the field of a lighting unit, and in particular to a lighting unit that is suitable for suspending from a ceiling, potentially being part of a suspended ceiling. More specifically, this present invention relates to a lighting interface component that provides an outlet or aperture for a device on a lighting tile, when the lighting tile is secured with the light interface component and being suspended from the ceiling.

BACKGROUND OF THE INVENTION

Ceilings come in a variety of different configurations these days, and one form that is quite common is a suspended ceiling, alternatively known as a dropped ceiling to provide a finished ceiling surface in a room or other architectural space. Often in pre-existing structures, a suspended ceiling may be installed at some level below an existing ceiling to conceal an older damaged ceiling and/or provide a new appearance in the architectural space in which the suspended ceiling is installed. In other applications, suspended ceilings may be installed in newly-constructed architectural spaces, based in part on their relative ease of installation. In one noteworthy aspect, a suspended ceiling typically permits piping, electrical and telephone wiring, and ductwork to be easily and conveniently concealed in an area between a pre-existing ceiling (or another architectural framework) and the suspended ceiling itself. This area above the suspended ceiling commonly is referred to as a plenum.

FIG. 1 depicts a conventional suspended ceiling employing a grid system 1020 (also referred to as "grid-work") of metal channels that are suspended on wires 1100 or rods 1120 from an overhead structure (typically a pre-existing ceiling or architectural framework). The metal channel as an interface component and in the form of a T-grid or T-bar comprises the grid system 1020 for providing the support needed to suspending the ceiling tiles 1080 and lighting tile 1000. The overhead structure is not explicitly shown in FIG. 1 to permit a view of the plenum, or the area above the suspended ceiling. The metal channels of the grid system 1020 are configured to form a regularly spaced grid (typically a 2 foot-by-2 foot or a 2 foot-by-4 foot pattern) of square or rectangular cells between the channels. The cells of the grid typically are filled with ceiling tiles or panels 1080 which drop into the grid system 1020. The tiles 1080 generally are formed of lightweight materials having a variety of finished surface textures and colors, and maybe particularly designed to facilitate acoustic or thermal isolation as well as fire safety. Once installed, the tiles 1080 may be easily removed and replaced to provide access as needed to the plenum 1140 (where there may be various wiring, pipes, and ductwork requiring repair or alteration).

WO2010042216 discloses a tile-based illumination system comprising T-bars, wherein the T-bars have through-holes enabling mechanical passages for conducting tabs.

SUMMARY OF THE INVENTION

There is a desire to provide further functionality for the interface component in the form of a T-grid or T-bar that comprises the grid system for the suspended ceiling. Especially when the interface component is supporting a lighting tile. This can be providing a solution for the operation of a device that is part of the lighting tile.

According to a first aspect, this and other objects are achieved by a lighting unit. The lighting unit for a suspended ceiling comprises one or more lighting tiles and an interface component. The interface component forms at least a portion of a grid system for the suspended ceiling and for supporting the lighting tile. The interface component comprises a central support portion having a first end facing a ceiling, and a second end having a first flange and a second flange that are opposing each other. And at least one of the first flange and the second flange comprises a through-hole that serves as an aperture for at least part of a device that is arranged at one of the peripheries of the lighting tile when the first flange is configured to support a first lighting tile when the first lighting tile is installed in the suspended ceiling and/or the second flange is configured to support a second lighting tile when the second lighting tile is installed in the suspended ceiling, wherein at least part of the device comprises one of (i) an ion generation source configured to, in operation, generate ionized air molecules in a physical area beneath the suspended ceiling, (ii) a sensor configured to, in operation, sense a change in a physical area beneath the suspended ceiling, and (iii) a light source configured to, in operation, emit light in a physical area beneath the suspended ceiling.

In the context of the present invention, the term 'central support portion' may be understood as an extended spine is a somewhat thin planar structure that extends along with the grid system of the suspended ceiling. The first and the second flanges, along with the central support portion may together form an inverted "T" to generally form the T-bar.

In the context of the present invention, the term 'flange' may be understood as an extension of the body of the central support portion that allows resting of the lighting tiles, as well as the ceiling tiles. The lighting tiles and/or the ceiling tiles may also be attached with the flange by means of screws or adhesive.

The interface component may be directly connected to the ceiling, or via wires or rods from the ceiling.

In the context of the present invention, the term 'through-hole' may be understood as a channel, a see-through channel through the flange.

In the context of the present invention, the term 'serves as an aperture' may be understood as a configuration where the device can see through the through-hole of the flange from one side of a flange to an other side of the flange, where one side of the flange is close to the ceiling and the other side of the flange is further away from the ceiling. Without the through-hole and aligning with the through-hole, the device would hide behind the flange.

In the context of the present invention, the term 'peripheries' may be understood as the longitudinal ends of the lighting tile. Alternatively, the region close to the edge surfaces of the lighting tile.

At least part of a device that is located at a periphery of the lighting tile is at least arranged to face the through-hole when the lighting tile is secured or supported by the flange. Therefore, such a device that is located at the periphery of the lighting tile can still function while being located behind the flange. As a result, the use of the effective area on the lighting tile is increased.

The lighting tile comprises the device e.g. the device is (partly) integrated or embedded in the lighting tile.

The one or more lighting tiles may comprise at least 5 lighting tiles, preferably at least 7 lighting tiles, more preferably at least 9 lighting tiles, most preferably at least 10 lighting tiles.

The through-hole may comprise a first aperture end facing the ceiling and a second aperture end opposite to the said first aperture end, and wherein at least part of the device is arranged in the through-hole from the first aperture end and/or to protrude from the second aperture end of the through-hole facing away from the ceiling.

The through-hole may comprise a first aperture end facing the ceiling and a second aperture end opposite to the said first aperture end, and wherein at least part of the device is arranged in the through-hole and/or wherein at least part of the device protrudes from the second aperture end facing away from the ceiling.

The through-hole may comprise a first aperture end facing the ceiling and a second aperture end opposite to the said first aperture end, and wherein at least part of the device at least partially extends into the through-hole from the first aperture end.

Also, the at least part of a device may be extended into the through-hole, between the first aperture end, or the second aperture end. This may help mechanically secure the lighting tile with the interface component.

Alternatively, the device especially the device end that is facing against the ceiling may flush with the first aperture end, or the second aperture end.

The through-hole has a diameter and the diameter can be between 0.5 to 2 centimeters.

The through-hole may have a dimension chosen from a range between 0.5 to 2 centimeters.

The through-hole may have a cylindrical shape.

The through-hole may taper out from the first aperture end towards the second aperture end, or taper in from the first aperture end towards the second aperture end.

The first aperture end and/or the second aperture end may have circumferences in the shape of a circle, ellipse, or rectangle.

At least part of the device may comprise an ion generation source configured to, in operation, generate ionized air molecules in a physical area beneath the suspended ceiling.

The at least part of the device may be configured to provide ionized air for the purpose of disinfection and neutralizing bad odor.

The device may be an air ionizer that provides positive and/or negative ions to disinfect the air and neutralize odor. The brush or needles as an ion generation source of the air ionizer may be located within the through-hole to prevent damage by mishandling.

The ionized air molecules may be generated in the lighting tile and expelled through the through-hole in the physical area beneath the suspended ceiling, and/or the ionized air molecules are generated in the through-hole in the physical area beneath the suspended ceiling, and/or the ionized air molecules are generated in the physical area beneath the suspended ceiling.

The brush or needles as an ion generation source of the air ionizer may extend out of the through-hole for providing sufficient flow of the ionized air.

The at least part of the device may comprise a sensor configured to, in operation, sense a change in a physical area beneath the suspended ceiling.

The at least part of the device may comprise a sensor device.

A sensor or a sensor device with a field of view access via the through-hole may be suitable for lighting tiles with concealed sensor functionality. This may be relevant from an aesthetic perspective.

The sensor may have at least one of a presence sensor, a temperature sensor, a humidity sensor, and a color sensor.

The sensor may be arranged in the lighting tile, in the through-hole and/or outside the through-hole in the physical area beneath the suspended ceiling.

At least part of the device may comprise a light source configured to, in operation, emit light in a physical area beneath the suspended ceiling.

The light source may be arranged in the lighting tile, in the through-hole and/or outside the through-hole in the physical area beneath the suspended ceiling.

The light source may be configured to emit visible light.

The light source may be configured to emit violet and/or ultra-violet (UV) light.

The lighting tile may comprise a closed UV disinfection system. The UV and/or violet light source may be arranged inside the lighting tile. Air from the physical area beneath the ceiling may be transferred into the lighting tile via an air inlet, a through-hole acting as an air inlet. The air is then disinfected by exposure to UV light. Subsequently, the disinfected air is expelled out the lighting tile via the air outlet into the physical area beneath the ceiling. Another through-hole acting as an air outlet.

The at least part of the device may be configured to emit at least one of violet light and ultra-violet light (i.e. UV-A, UV-B and/or UV-C).

Violet light is light in the wavelength range from 380 to 420 nm.

There are three types of ultra-violet (UV) light classifications based on their wavelength: UV-A (315 to 380 nm), UV-B (280 to 315 nm), and UV-C (100 to 280 nm).

The through-hole may be configured for guiding light.

In this case, the through-hole may have a light reflective layer or coating in an inner wall of the through-hole for facilitating the light guide function.

The at least part of the device may comprise a guide for guiding light, and wherein at least part of the guide may be arranged in the through-hole from the first aperture end, and/or may protrude from the second aperture end of the through-hole.

The at least part of the device may comprise a guide for guiding light, and maybe arranged in the through-hole and/or wherein at least part of the guide may protrude from the through-hole facing away from the ceiling.

The at least part of the device may comprise a guide for guiding light that is configured at and/or through the through-hole.

In this case, the guide may be a light guide, an optical fiber.

The light guide may be made from an inorganic material e.g. quartz, sapphire, glass, ceramics.

The light guide may be made from an organic material e.g. PMMA.

A light guide may carry the light out of the second aperture end from the device, and/or transmit light collected from the second aperture end towards the device.

The lighting unit may comprise an optical element that is arranged at the second aperture end.

An optical element may efficiently direct light from the second aperture end, or collect light from the second aperture end with desired conditions. Therefore, the optical element may be a lens such as a wide viewing angle lens, a segmented lens, a TIR lens, or a collimating lens. Alternatively, the optical element may be a reflector type optics.

The optical element may be mechanically fixed or form a single body with the (interface component of the) grid system.

The through-hole may comprise an inner wall that comprises a non-absorptive material.

The through-hole may comprise an inner wall that comprises a UV non-absorptive material.

In the context of the present invention, a 'non-absorptive material' may be referred to as a material that is reflective and/or translusive towards UV and/or violet light.

If reflective, the reflectivity of the inner wall may be at least 70% for the violet and/or UV light emitted by the said light source, preferably at least 80%, more preferably at least 85%, most preferably at least 90%.

The interface component may be made from a non-absorptive material.

The interface component may be made from a UV non-absorptive material.

The materials used in the interface component may be susceptible to degradation by the UV and violet light. To protect the interface component, the through-hole may be made from UV non-absorptive materials. For example, polytetrafluoroethylene (PTFE) or similar Teflon synthetics are reflective (potentially 90 to 95%) towards UV light. Alternatively, the inner wall of the through-hole may be coated with similar UV-reflective materials.

The through-hole may be configured as an air inlet and/or an air outlet.

The lighting unit e.g. the lighting tile may comprise a fan. The fan may be used to create a forced fluid (forced draft) e.g. airflow. For example, air can be transferred into the air inlet into the lighting tile and expelled from the lighting tile via the air outlet into the physical area.

The lighting unit may comprise a tube or an orifice that is arranged at the second aperture end.

Carefully chosen tube or orifice may promote and/or control the flow of air via the through-hole channel.

The through-hole of the interface device may provide an air channel for the air inlet and/or outlet for the at least part of the device. This may help promote air circulation for the lighting tile or the environment near the lighting tile.

The interface component may be shaped as a well-known T-grid.

The lighting tile may be configured to provide white light having a correlated color temperature in a range from 2000 to 8000 K and a color rendering index CRI of at least 80.

The lighting tile is suitable for emitting color tunable visible light for illuminating a space and/or provide ambiance lighting.

The lighting tile may comprise an array of LED or LED strips.

The lighting tile may comprise at least two devices arranged at distance from each other.

The devices may be arranged at the peripheries of the lighting tile, while the lighting emitting devices such as an LED array may be located between the devices.

According to a second aspect of the present invention, a lighting system is provided comprising the lighting unit and a plurality of ceiling tiles, wherein the interface component supports the lighting tiles and ceiling tiles.

The interface device can be useful for supporting the lighting tiles and the ceiling tiles alike and can be the basis for realizing at least a portion of a grid system of the lighting system, similar to the grid system known for suspended ceilings. For lighting tile, however, the interface device can provide additional functionality according to the present invention.

It should be understood that the interface component having a through-hole may not always receive a functional device either from a lighting tile or a ceiling tile. Also, one may assume the device facing or extending through the through-hole of the interface component may not be a functional device, yet shaped and appearing as a functional device.

For example, a dummy device.

It is noted that the invention relates to all possible combinations of features recited in the claims. Other objectives, features, and advantages of the present inventive concept will appear from the following detailed disclosure, from the attached claims as well as from the drawings. A feature described in relation to one of the aspects may also be incorporated in the other aspect, and the advantage of the feature is applicable to all aspects in which it is incorporated.

BRIEF DESCRIPTION OF THE DRAWINGS

The above, as well as additional objects, features, and advantages of the disclosed devices, methods, and systems, will be better understood through the following illustrative and non-limiting detailed description of embodiments of devices, methods, and systems, with reference to the appended drawings, in which.

As illustrated in the figures, the sizes of layers and regions are exaggerated for illustrative purposes and, thus, are provided to illustrate the general structures of embodiments of the present invention. Like reference numerals refer to like elements throughout.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled person.

Figure 1:
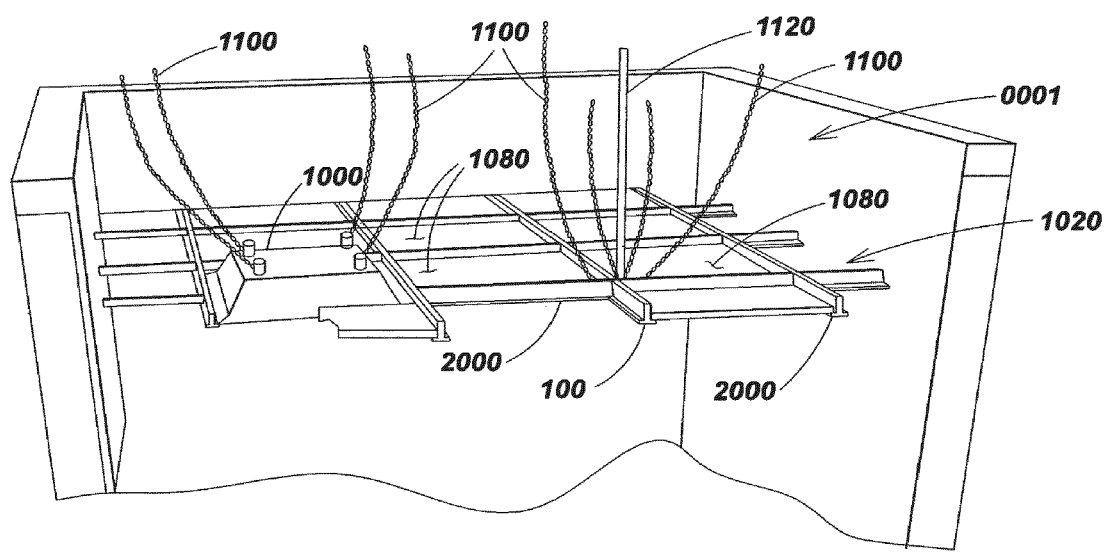
FIG. 1 generally illustrates a typical suspended ceiling implementation.
Figure 2:
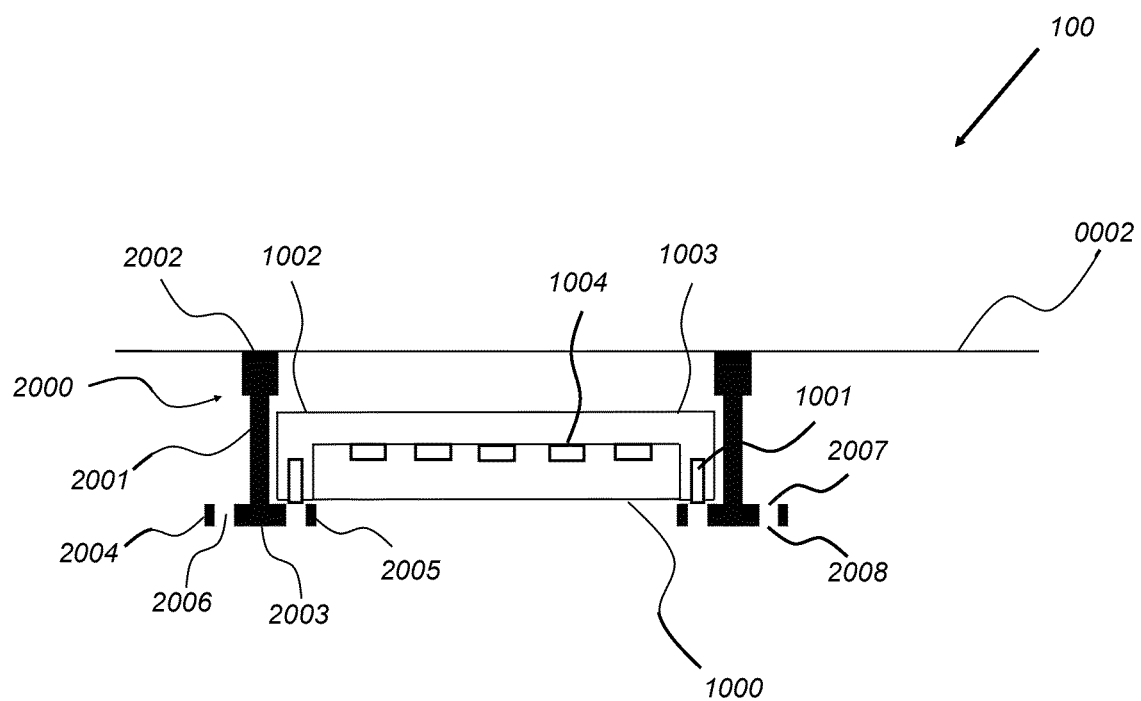
FIG. 2 shows a cross-sectional view of a lighting unit.

Referring initially to FIG. 2, a cross-sectional view of a lighting unit 100 is shown. The lighting unit 100 comprises a lighting tile 1000. The lighting tile 1000 comprises two devices 1001 that are located at the peripheries 1002, 1003 of the lighting tile 1000. The peripheries 1002 and 1003 are longitudinal ends of the lighting tile 1000. The lighting tile 1000 comprises multiple LED light sources 1004. The skilled person may also consider other forms of light sources other than LED light sources 1004. In FIG. 2, one lighting tile 1000 is shown, however, the lighting unit 100 is not limited to a single lighting tile 1000.

The lighting unit 100 further comprises an interface component 2000 that comprises a central support portion 2001 as a spine having a first end 2002 that is attached to the ceiling 0002. And a second end 2003 of the central support portion has a first flange 2004 and a second flange 2005 that are opposing each other. The interface component 2000 is depicted as a T-bar or T-grid element is typically found as the grid system for the suspended ceiling. The first flange 2004 and the second flange 2005 are configured to support the lighting tile 1000 as the peripheries 1002, 1003 are resting on the first and the second flanges 2004, 2005. Additionally, the first flange 2004 and the second flange 2005 comprises through-holes 2006 that serve as apertures for the device 1001 that are arranged at the peripheries 1002, 1003 of the lighting tile 1000. The through-hole 2006 offers a field of view for at least part of the device 1001. The through-hole 2006 offers a field of view for at least part of the device 1001. In FIG. 2, the devices 1001 are configured such that the device 1001 is facing the through-hole 2006, opposite to a direction of the ceiling 0002.

In FIG. 2, the through-hole 2006 is shown to have a first aperture end 2007 that is facing the ceiling 0002 and a second aperture end 2008 opposite to the said first aperture end 2007. The device 1001, especially the end of the device that is facing against the ceiling 0002 is configured to flush with the first aperture end 2007.

The device or at least part of the device that has an aperture through the through-hole may be a light source that emits, for example, violet or ultra-violet light. The device or at least part of the device may also emit visible light. The device or at least part of the device may comprise a sensor. The sensor may be a presence sensor, for example, based on infrared detection. The sensor device may also be a color sensor or ambiance sensor (temperature and/or humidity sensor).

The interface component may be made from UV non-absorptive material or at least the through-hole coated with UV non-absorptive material, for example, polytetrafluoroethylene (PTFE) or similar Teflon synthetics that are reflective towards UV light.

The device or at least part of the device that has an aperture through the through-hole may be an optoelectronic device that is configured to emit photons given electric signal or power, or produce electrons when exposed to photons. Therefore, the device can be an emitter of light or photons, or a sensor based on light sensitivity.

Figure 3:
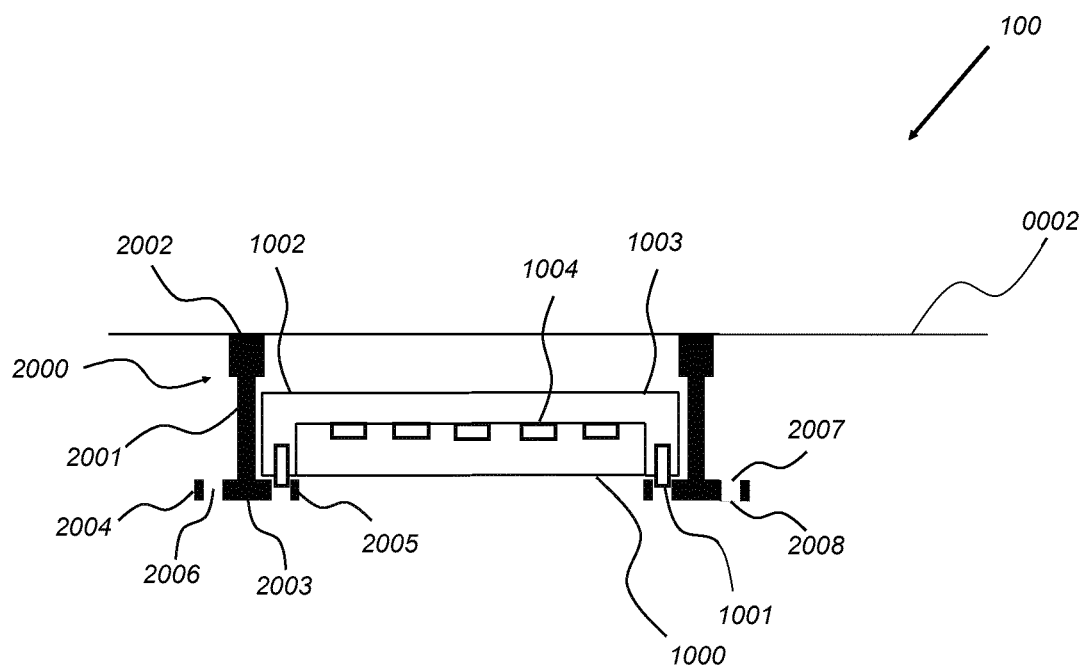
FIG. 3 shows a cross-sectional view of an alternative configuration for the lighting unit.

FIG. 3 shows a cross-section of the lighting unit 100 with a different configuration for the device 1001. FIG. 3 shares the same component and component numerals as shown in FIG. 2. Except, it is shown that at least part of a device 1001 at least partially extends into the through-hole 2006 from the first aperture end 2007. The at least part of a device may be extended into the through-hole, between the first aperture end, or the second aperture end. By changing the extension of at least part of a device in the through-hole, one may realize a change in a field of view for the device. The at least part of a device may be extended beyond and through the second aperture end. This may help mechanically secure the lighting tile with the interface component.

Figure 4:
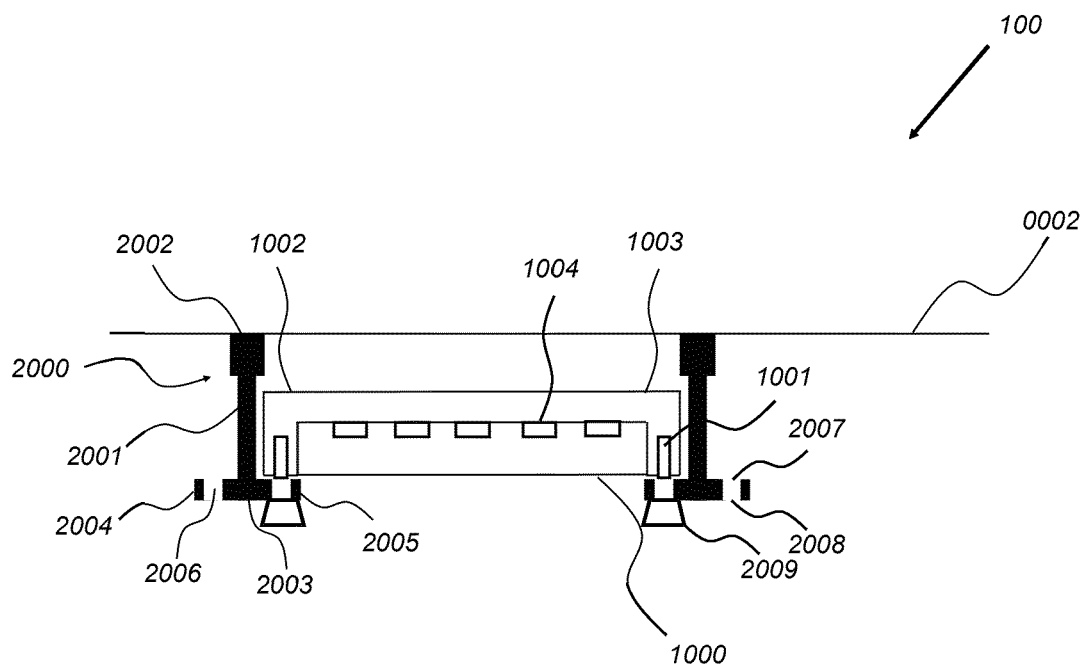
FIG. 4 shows a cross-sectional view of an alternative configuration for the lighting unit.

FIG. 4 shows a cross-sectional view of an alternative configuration for the lighting unit 100. FIG. 4 shares the same component and component numerals as shown in FIG. 2. Except, it is shown that an optical element 2009 that is arranged at the second aperture end 2008 of the through-hole 2006. An optical element 2009 may offer advantageous manipulation of light going out of the second aperture end 2008 or coming into the second aperture end 2008. For example, a wide viewing angle lens at the second aperture end 2008 may offer a collection of light with wide viewing angles. The optical element may be a lens such as a wide viewing angle lens, a segmented lens, a TIR lens, or a collimating lens. Alternatively, the optical element may be a reflector type optics.

Figure 5:
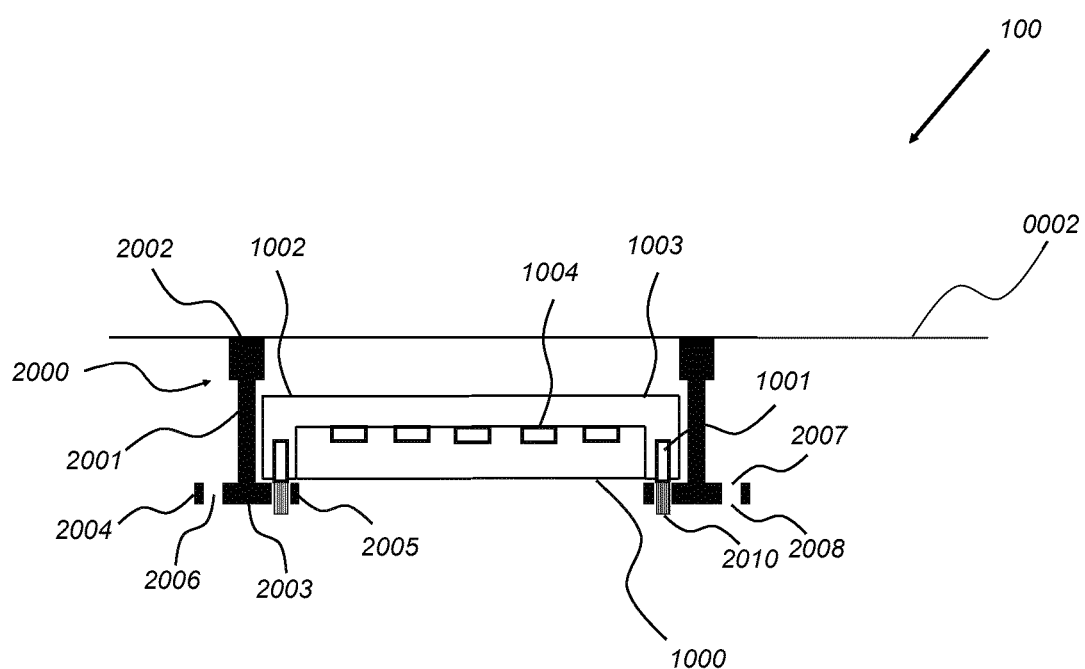
FIG. 5 shows a cross-sectional view of a lighting unit having a light guide in the through-hole.

FIG. 5 shows a cross-sectional view of a lighting unit 100. FIG. 4 shares the same component and component numerals as shown in FIG. 2. Except, it is shown that the end of the device that is facing against the ceiling 0002 that is configured to flush with the first aperture end 2007 further comprises a guide 2010 for guiding light that extends through the through-hole 2010. The guide 2010 can be an optical fiber or similar that offers a total internal reflection of light and transmission of light from one end to other. Hence, the light guide may offer efficient transmission of light. Alternatively, the through-hole may have a reflective inner wall that facilitates a light guiding effect.

Figure 6:
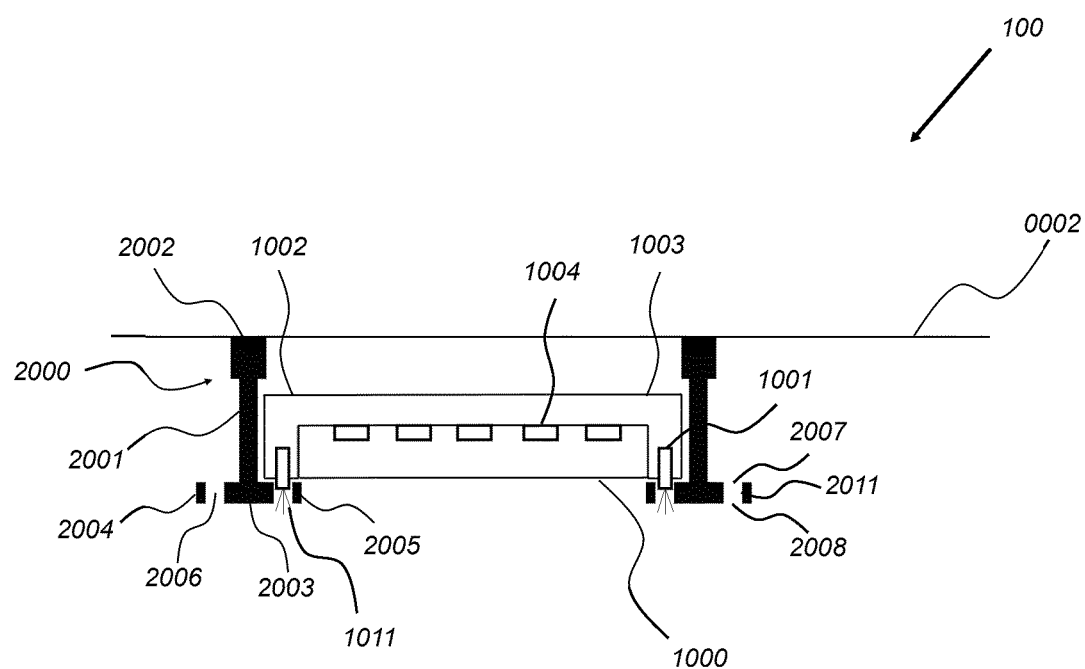
FIG. 6 shows a cross-sectional view of a lighting unit having an air ionizer.

FIG. 6 shows a cross-sectional view of a lighting unit 100 where the device or at least part of the device 1001 is configured to act as an air ionizer. FIG. 6 shares the same component and component numerals as shown in FIG. 3. The device 1001 comprises ion generation source 1011 as indicated by needles or brushes that are configured through the through-hole 2006. The ion generation source 1011 may also completely extend out of the second aperture end 2008 which may promote flow of ionized air. Alternatively, the ionizer or the ion generation source 1011 may be located behind the first aperture end 2007, on a side of the lighting tile 1000 close to the ceiling 0002. In this case, the through-hole may serve as an air inlet and/or air outlet for carrying air towards the air ionizer and/or carrying ionized air from the air ionizer.

Figure 7:
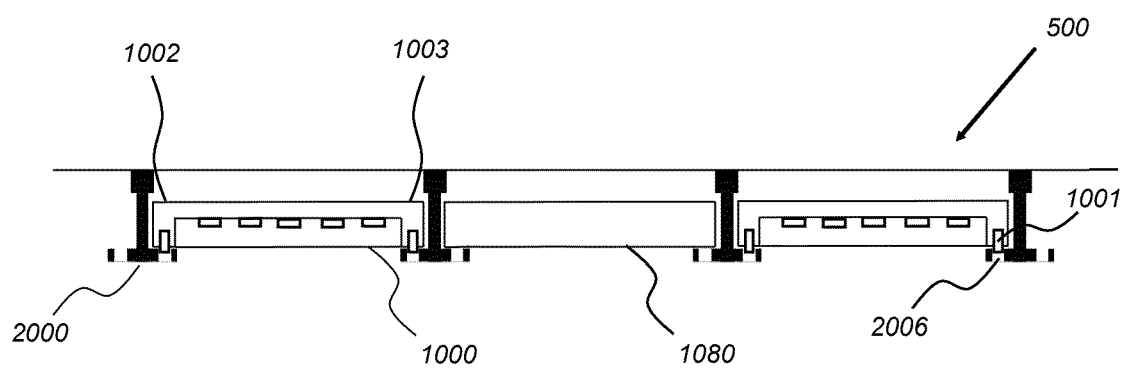
FIG. 7 shows a cross-sectional view of a lighting system.

FIG. 7 shows a cross-sectional view of a lighting system 500. The lighting system 500 comprises lighting tiles 1000 and a ceiling tile 1080. The lighting system 500 comprises multiple interface components 2000 that are supporting the lighting tiles 1000 and ceiling tile 1080. The interface components 2000 forms at least a portion of the grid system for the suspended ceiling In addition to providing support for the lighting tile 1000 and the ceiling tile 1000, the through-hole 2006 of the interface component 2000 serves as an aperture for the device or at least part of the device 2006 that is located to one of the peripheries 1002, 1003 of the lighting tile 1080. Therefore, the interface component 2000 may form a grid system for the lighting system 500, similar to the grid system known for suspended ceilings.

It should be noted that the above-mentioned embodiments illustrate rather than limit the invention and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements.

The mere fact that certain features are recited in mutually different dependent claims does not indicate that a combination of these features cannot be used to advantage. The various aspects discussed above may be combined in order to provide additional advantages. Further, the person skilled in the art will understand that two or more embodiments may be combined.

The invention claimed is:

1. A lighting unit for a suspended ceiling comprising:
   one or more lighting tiles;
   an interface component that forms at least a portion of a grid system for the suspended ceiling and for supporting the one or more lighting tiles;
   wherein the interface component comprises a central support portion having a first end facing a ceiling, and a second end having a first flange and a second flange that are opposing each other; and
   wherein at least one of the first flange and the second flange comprises a through-hole that serves as an aperture for at least part of a device that is arranged at one of the peripheries of the lighting tile when the first flange is configured to support a first lighting tile when the first lighting tile is installed in the suspended ceiling and/or the second flange is configured to support a second lighting tile when the second lighting tile is installed in the suspended ceiling,
   wherein at least part of the device comprises one of:
     an ion generation source configured to, in operation, generate ionized air molecules in a physical area beneath the suspended ceiling,
     a sensor configured to, in operation, sense a change in a physical area beneath the suspended ceiling, and
     a light source configured to, in operation, emit light in a physical area beneath the suspended ceiling.

2. The lighting unit according to claim 1, wherein the through-hole comprises a first aperture end facing the ceiling and a second aperture end opposite to the said first aperture end, and wherein at least part of the device is arranged in the through-hole from the first aperture end, and/or to protrude from the second aperture end of the through-hole.

3. The lighting unit according to claim 1, wherein the light source is configured to emit violet and/or ultra-violet (UV) light.

4. The lighting unit according to claim 1, wherein the at least part of the device comprises one of sensor and the light source, wherein the through-hole is configured for guiding light.

5. The lighting unit according to claim 1, wherein the at least part of the device comprises one of sensor and the light source, wherein the at least part of the device comprises a guide for guiding light, and wherein at least part of the guide is arranged in the through-hole from the first aperture end, and/or to protrude from the second aperture end of the through-hole.

6. The lighting unit according to claim 1, wherein the at least part of the device comprises one of sensor and the light source, and wherein the lighting unit comprises an optical element that is arranged at the second aperture end.

7. The lighting unit according to claim 3, wherein the through-hole comprises an inner wall that comprises a non-absorptive material.

8. The lighting unit according to claim 3, wherein the interface component is made from a non-absorptive material.

9. The lighting unit according to claim 1, wherein the through-hole is configured as an air inlet and/or an air outlet.

10. The lighting unit according to claim 1, wherein the interface component is a T-grid.

11. The lighting unit according to claim 1, wherein the lighting tile is configured to provide white light having a correlated color temperature in a range from 2000 to 8000 K and a color rendering index (CRI) of at least 80.

12. A lighting system comprising the lighting unit according to claim 1 and a plurality of ceiling tiles, wherein the interface component supports the lighting tiles and ceiling tiles.

* * * * *